(12) United States Patent
Koetje

(10) Patent No.: US 12,714,326 B2
(45) Date of Patent: Aug. 25, 2026

(54) APPARATUS FOR DETECTING ELECTRICAL CONDUCTIVITY

(71) Applicant: Actegy Limited, Bracknell (GB)

(72) Inventor: Anno Jakob Koetje, Guildford (GB)

(73) Assignee: Actegy Limited, Bracknell (GB)

( * ) Notice: Subject to any disclaimer, the term of this patent is extended or adjusted under 35 U.S.C. 154(b) by 697 days.

(21) Appl. No.: 18/041,544

(22) PCT Filed: Aug. 10, 2021

(86) PCT No.: PCT/GB2021/052061

§ 371 (c)(1),
(2) Date: Feb. 13, 2023

(87) PCT Pub. No.: WO2022/038336

PCT Pub. Date: Feb. 24, 2022

(65) Prior Publication Data

US 2023/0371838 A1 Nov. 23, 2023

(30) Foreign Application Priority Data

Aug. 20, 2020 (GB) ..................................... 2012999

(51) Int. Cl.

| | |
|---|---|
| ***A61B 5/0537*** | (2021.01) |
| ***A61B 5/00*** | (2006.01) |
| ***A61N 1/08*** | (2006.01) |
| ***A61N 1/36*** | (2006.01) |

(52) U.S. Cl.

CPC .......... *A61B 5/0537* (2013.01); *A61B 5/4875* (2013.01); *A61N 1/36003* (2013.01); *A61N 1/3603* (2017.08); *A61N 2001/083* (2013.01)

(58) Field of Classification Search

None
See application file for complete search history.

(56) References Cited

U.S. PATENT DOCUMENTS

2005/0177060 A1* 8/2005 Yamazaki ............ A61B 5/0537 600/547
2013/0331907 A1* 12/2013 Sumners .............. A61N 1/0472 607/144
2016/0374618 A1* 12/2016 Giovangrandi ...... A61B 5/0537 600/393

FOREIGN PATENT DOCUMENTS

WO WO-2019134033 A2 * 7/2019 ............... A61B 5/01

* cited by examiner

*Primary Examiner* — Mallika D Fairchild
(74) *Attorney, Agent, or Firm* — Saunders McKeon PLLC

(57) ABSTRACT

Apparatus (30) for detecting motion of a device (1) for electrical stimulation of a subject is described. The apparatus (30) comprises a motion detector (2) to detect the motion of the device (1) and generate a motion output signal in response to the detected motion. The motion output signal is indicative of the amount of detected motion. A processor (21) is coupled to the motion detector (20). The processor (21) receives (72) the motion output signal from the motion detector (20) and generates a first processor output signal in response to the received motion output signal. An output device (14, 26) is coupled to the processor (21). The output device (14, 26) receives the first processor output signal from the processor (21) and generates a first output signal in response to the received first processor output signal. The processor (21) generates the first processor output signal if either: (i) the received motion output signal is greater than a threshold; or (ii) the received motion output signal is less than a threshold.

16 Claims, 8 Drawing Sheets

APPARATUS FOR DETECTING ELECTRICAL CONDUCTIVITY

The invention relates to apparatus for detecting electrical conductivity and especially for detecting electrical conductivity between a subject and a device for electrical stimulation of the subject.

The electrical stimulation of a subject for improving circulation is known. In particular, the electrical stimulation of the feet and legs of a subject to improve venous blood flow is known and reported in the art. For example, Kaplan, R. E. et al., 'Electrical foot stimulation and implications for the prevention of venous thromboembolic disease', (Thrombosis and haemostasis, 2002, vol. 88, no2, pages 200 to 204) describe the results of experiments conducted on subjects, in which mild electrical stimulation was applied to the calf or plantar muscles of the subject. Analysis showed an increase in the venous femoral and popliteal blood flow of the side of the subject to which electrical stimulation was applied, compared with the non-stimulated side.

Further, W Man, I. O., et al. 'Effect of neuromuscular electrical stimulation on foot/ankle volume during standing' (Med Sci Sports Exerc., 2003, April, 35(4), pages 630 to 634) report that the neuromuscular electrical stimulation of the lower leg muscles of a subject prevented the increase in volume of the feet and ankles generally experienced after extended periods of standing. It was concluded that neuromuscular electrical stimulation provided a means for reducing swelling in the lower limbs of subjects that are not capable of fully activating their musculo-venous pumps.

Faghri, P. D., et al., 'Electrical stimulation-induced contraction to reduce blood stasis during arthroplasty' (IEEE Trans Rehabil Eng., 1997, March, 5(1), pages 62 to 69) report data suggesting that continuous electrical stimulation-induced contractions could improve lower leg circulation in subjects by eliciting the physiologic muscle pump. This will lead, in turn, to improved venous circulation and a reduction of blood stasis, for example during total hip and/or knee surgery. The authors suggest this technique may offer greater protection against deep vein thrombosis (DVT) and pulmonary embolism (PE) during surgery than the commonly used sequential compression devices and techniques.

Faghri, P. D., et al., 'Venous hemodynamics of the lower extremities in response to electrical stimulation' (Arch Phys Med Rehabil., 1998, July, 79(7), pages 842 to 848) concluded from experiments conducted that periodic single electrostimulation-induced calf muscle contractions produced significant muscle pump function and could be used to improve venous blood flow and reduce stasis in the lower leg, while continuous electrostimulation-induced contractions could improve lower leg peripheral perfusion while eliciting the physiologic venous muscle pump.

Anderson, S. I., et al., 'Chronic transcutaneous electrical stimulation of calf muscles improves functional capacity without inducing systemic inflammation in claudicants' (Eur J Vasc Endovasc Surg., 2004, February, 27(2), pages 201 to 209) report that chronic electrical muscle stimulation is an effective treatment for alleviating intermittent claudication. The technique, by targeted activation of a small muscle mass, does not engender a significant systemic inflammatory response.

A method of neuro-muscular stimulation for the prevention of venous thrombosis and pulmonary embolism is disclosed in U.S. Pat. No. 5,358,513. The method comprises applying electrical stimulation to the subject by means of electrodes attached to an anterior portion of the subject's knee immediately proximal the common peroneal nerve. The electrical stimulation is applied as trains of pulse modulated sinusoids.

More recently, U.S. Pat. No. 6,615,080 discloses the neuroelectrical stimulation of the foot muscles of a subject for the prevention of deep vein thrombosis (DVT), pulmonary embolism (PE) and lower extremity edema. The method comprises applying electrical pulses to the muscles of the foot, in particular in a square wave pattern of variable frequency, duration, intensity, ramp time and on-off cycle. The electrical stimulation is applied to the soles of the feet of the subject, to reduce the pooling of blood in the soleal veins.

Devices for the electrical stimulation of a subject are known and are commercially available. In particular, devices for applying electrical stimulation to the feet of subjects, especially to the plantar muscles, are known and commercially available. One example of such a device is the REVITIVE® Circulation Booster™ available from Actegy Limited in the United Kingdom and described in UK Patent Application No. 2493904.

The device disclosed in GB2493904A comprises a circular disc with a pair of electrical contact pads on one side of the disc and a rocker element on the opposite side. In use, the user places their feet on the pads and the rocker element contacts the floor or ground so that the device can rock backwards and forwards on the rocker element. Electrical stimulation of a variable intensity is then provided through the pads to the plantar muscles of the feet of the user to cause repeated contraction and relaxation of the leg muscles of the user. The advantage of the rocker element is that it allows the disc to rock (or pivot) forwards and backwards thereby permitting a user's feet to move about the ankle joint during the electrical stimulation cycle.

However, it has been realised that the effectiveness of the electrical stimulation can be significantly affected by the electrical conductivity between the user's feet and the electrical contact pads. In extreme cases it has been found that where the electrical conductivity is low, the effectiveness of the electrical stimulation can be minimal or even non-existent.

In accordance with a first aspect of the present invention, there is provided apparatus for detecting electrical conductivity between a subject and a device for electrical stimulation of the subject, the apparatus comprising:

(i) a first electrical contact adapted to contact skin of a subject in a first location, in use;

(ii) a second electrical contact adapted to contact the skin of the subject in a second location, in use;

(iii) a processor having an output coupled to the first electrical contact and an input coupled to the second electrical contact;

(iv) an output device coupled to the processor; and wherein the processor is configured to output an alternating voltage signal to the first electrical contact and to receive a response signal from the second electrical contact; and the processor being further configured to either: (a) send an output signal to the output device in response to the received response signal, the output signal corresponding to the received response signal and being indicative of the electrical conductivity between the device and the subject, in use; or (b) send an output signal to the output device if a voltage amplitude of the response signal received by the processor is below a threshold, the output signal being indicative that the electrical conductivity between the subject and the device is below the threshold.

In accordance with a second aspect of the present invention, there is provided a method of detecting electrical conductivity between a subject and a device for electrical stimulation of the subject, the method comprising:

(i) contacting a first electrical contact against skin of a subject in a first location;

(ii) contacting a second electrical contact against the skin of the subject in a second location;

(iii) applying an alternating voltage signal to the first electrical contact;

(iv) receiving a response signal at the second electrical contact; and wherein a processor is configured to output an alternating voltage signal to the first electrical contact and to receive a response signal from the second electrical contact; and the processor being further configured to either: (a) send an output signal to the output device in response to the received response signal, the output signal corresponding to the received response signal and being indicative of the electrical conductivity between the device and the subject, in use; or (b) send an output signal to the output device if a voltage amplitude of the response signal received by the processor is below a threshold, the output signal being indicative that the electrical conductivity between the subject and the device is below the threshold.

The output device may comprise at least one of: a visual display device; an audible signal output device; a haptic signal output device; and a wireless data signal output device. The wireless data signal output device may operate on one or more wireless network protocols, such as Bluetooth® or Wi-Fi based on the IEEE 802.11 family of standards. For example, the wireless data signal output device may comprise a Bluetooth® transmitter.

In one example of the invention, where the output device comprises a wireless data signal output device, the wireless data signal output device may be adapted to be coupled to a mobile device, such as a smartphone or tablet, by a wireless transmission link, in use.

Preferably, the mobile device comprises at least one of: a visual display device; an audible signal output device; and a haptic signal output device. The at least one of the visual display device, the audible signal output device and the haptic signal output device is adapted to generate a user output signal in response to the output signal received by the mobile device from the processor via the wireless data signal output device.

Typically, the alternating voltage signal may comprise a square wave voltage signal.

Preferably, the alternating voltage signal has an amplitude of less than approximately 20V, more preferably, an amplitude of less than approximately 10V, even more preferably, an amplitude of less than or equal to approximately 5V and most preferably, an amplitude of from 1V to 5V.

Typically, the threshold corresponds to an amplitude of the response signal that is less than 50% of the output alternating voltage signal, preferably less than 35% of the output alternating voltage signal, more preferably less than 30% of output alternating voltage signal. Most preferably, the threshold corresponds to an amplitude of the response signal that is between 20% and 30% of the output alternating voltage signal. In one example, the threshold may correspond to an amplitude of the response signal that is between 23% and 26% of the output alternating voltage signal.

In one example of the invention, where the amplitude of the output alternating voltage signal is substantially 3V, the threshold corresponds to an amplitude of the response signal that is approximately in the range 0.7V to 0.8V.

Preferably, the apparatus is adapted such that the first and second electrical contacts are adapted to contact the skin of the subject such that the first and second locations are on different limbs of the subject. More preferably, the first and second locations are on different lower limbs of the subject, even more preferably the first and second locations may be on different lower legs of the subject, and most preferably on different feet of the subject. In one example of the invention, the first and second locations may be on plantar surfaces of different feet of the subject.

In accordance with a third aspect of the present invention, there is provided a device for electrical stimulation of a subject, the device comprising apparatus in accordance with the first aspect and optionally any features of the first aspect; and electrical stimulation means that is adapted to apply an electrical stimulation voltage to muscles of a body part of the subject, in use.

The processor may have an output that is coupled to the electrical stimulation means to enable the processor to control the electrical stimulation voltage. Alternatively, the device may further comprise another processor coupled to the electrical stimulation means to control the electrical stimulation voltage.

Typically, the electrical stimulation means are adapted to stimulate the muscles of a limb of a subject. Preferably, the electrical stimulation means are adapted to stimulate the muscles of a lower limb of a subject, such as at least one of the leg and foot muscles of a subject.

Typically, the electrical stimulation means comprises a first electrical stimulation contact surface and a second electrical stimulation contact surface. Typically, the first and second electrical stimulation contact surfaces are electrically isolated from each other. Preferably, the first and second electrical stimulation contact surfaces are adapted to contact a first and a second limb, respectively of a subject, in use. In one example of the invention, the first and second electrical stimulation contact surfaces are adapted to contact a first foot and a second foot, respectively of a subject, in use.

The device may comprise a housing. The first and second electrical stimulation contact surfaces may be located on an external portion of the housing.

Preferably, the first and second electrical contacts are located on an external surface of the device. More preferably, the first electrical contact is located on the first electrical stimulation contact surface and the second electrical contact is located on the second electrical stimulation contact surface. Even more preferably, the first and second electrical contacts are located within or inset into the respective first and second electrical stimulation contact surfaces.

Preferably, at least a portion of a contact surface of the first and second electrical contacts protrudes outwardly from a plane defined by the respective first and second electrical stimulation contact surfaces. Hence, at least a portion of the contact surface of the first and second electrical contacts is raised above the level of the respective first and second electrical stimulation contact surfaces Typically, the first and second electrical contacts are electrically isolated from the respective first and second electrical stimulation contact surface. The first and second electrical contacts may be encircled by an electrical insulating material to electrically isolate them from the respective first and second electrical stimulation contact surfaces.

Typically, the electrical stimulation means further comprises an electrical voltage supply device electrically coupled to the first and second electrical stimulation contact surfaces and adapted to apply an electric voltage across the first and second electrical stimulation contact surfaces.

Preferably, the electrical voltage supply device outputs an alternating electrical voltage waveform across the first and second electrical stimulation contact surfaces. More preferably, the electric voltage applied across the first and second electrical stimulation contact surfaces by the electrical supply device comprises a plurality of voltage pulses.

Preferably, the device further comprises a pivot member, the pivot member being adapted to permit the device to pivot around the pivot member in response to motion of the body part.

In accordance with a fourth aspect of the invention, there is provided a system comprising either: (i) apparatus in accordance with the first aspect; or (ii) a device in accordance with the third aspect; and a remote device comprising a remote wireless data input device and a remote output device; wherein the output device comprises a wireless data output device and the first output signal comprises a wireless data signal emitted by the wireless data output device; and the remote wireless data input device is adapted to receive the wireless data signal and the remote output device generates a remote user output signal in response to the received wireless data signal.

The remote wireless data signal input device may operate on one or more wireless network protocols, such as Bluetooth® or Wi-Fi based on the IEEE 802.11 family of standards. For example, where the wireless data output device comprises a Bluetooth® transmitter, the remote wireless data input device may comprise a Bluetooth® receiver.

The remote user output signal generated by the remote device may be at least one of: a visual output signal; an audible output signal; and a haptic output signal.

Typically, the remote device comprises a remote device processor coupled to the wireless data input device and the remote output device, the processor generates a remote device processor output signal in response to the received wireless data signal, and the remote output device receives the remote device processor output signal and generates the remote user output signal in response to the remote device processor output signal.

Typically, the remote device is a mobile device and the remote user output signal generated by the mobile device is generated and displayed on a user interface of the mobile device by application software on the mobile device.

The term "mobile device" as used herein means any portable electronic device having a wireless receiver and a user interface including a display, and includes (but is not limited to) smartphones, tablets and laptop computers.

Preferably, the remote device comprises a remote user input device which is adapted to receive an input from a user and a remote wireless data output device; in response to a received input from a user on the remote user input device, the remote device being adapted to transmit a remote user input signal to the apparatus, the apparatus comprising a wireless data input device adapted to receive a remote user input signal transmitted by the remote wireless data output device, the processor and/or the other processor being adapted to receive the remote user input signal from the wireless data input device.

Where the remote device comprises a user interface, the user interface may be adapted to display the remote user output signal and to receive the user input.

Typically, the processor or other processor controls the electrical stimulation voltage in response to the received remote user input signal, in use.

Preferably, the wireless data output devices and wireless data input devices are each integrated into a single device, such as a wireless transceiver. For example, the transceivers may comprise Bluetooth® transceivers.

Where the system comprises a device in accordance with the second aspect, the processor output signal may be sent by the processor to the output device and another output device on the device, the other output device comprising at least one of a visual display device; an audible signal output device; and a haptic signal output device.

An advantage of the invention, is that the inventors have realised that it is possible to indicate to a user whether the level of electrical conductivity between the subject and the first and electrical contacts is sufficient for electrical stimulation depending on whether the amplitude a received voltage signal is above or below a threshold.

An example of apparatus for and a method of detecting electrical conductivity will now be described with reference to the accompanying drawings, in which.

Figure 1:
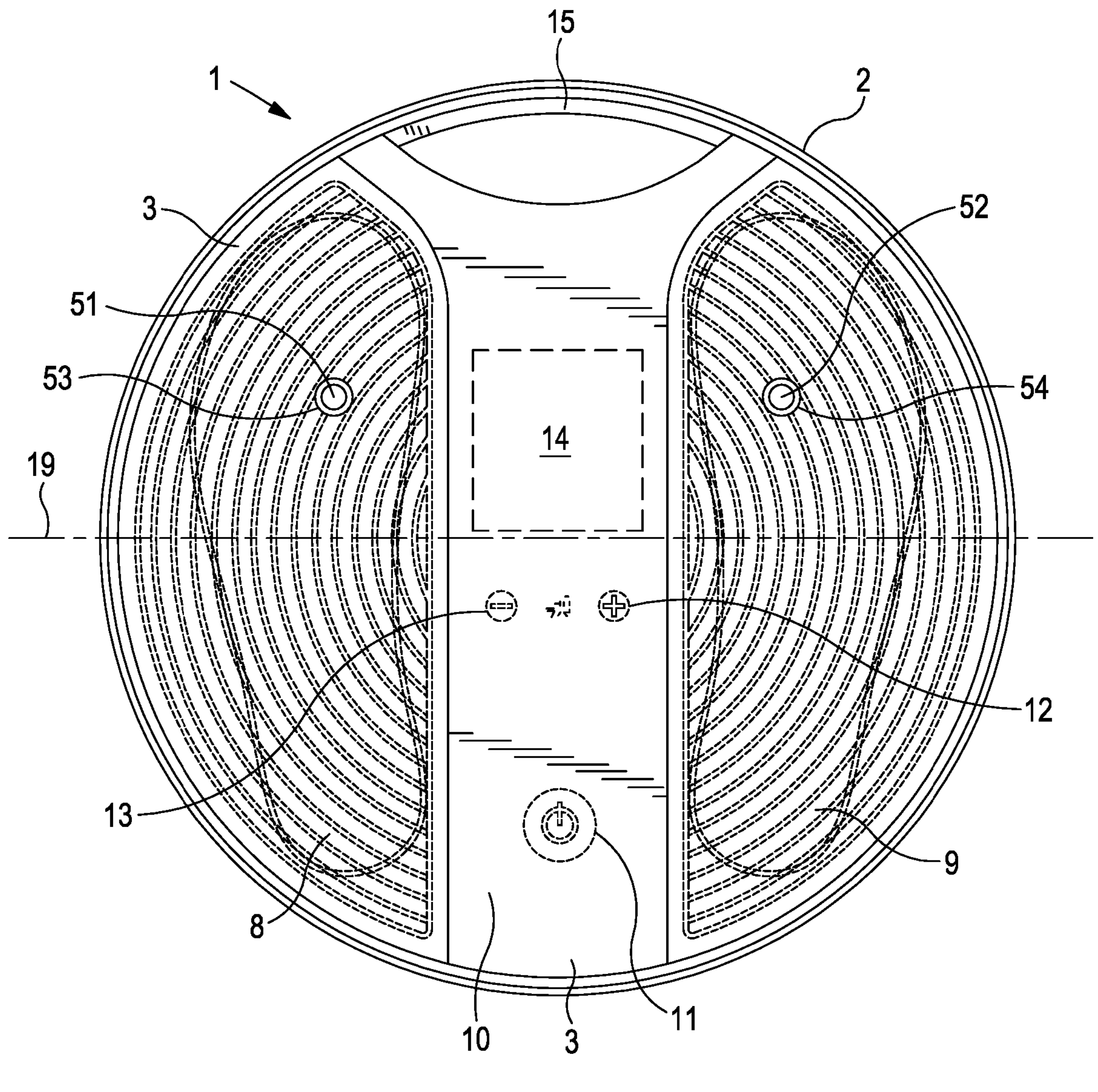
FIG. 1 is a plan view of a device for electrical stimulation of a subject incorporating apparatus for detecting electrical conductivity.
Figure 2:
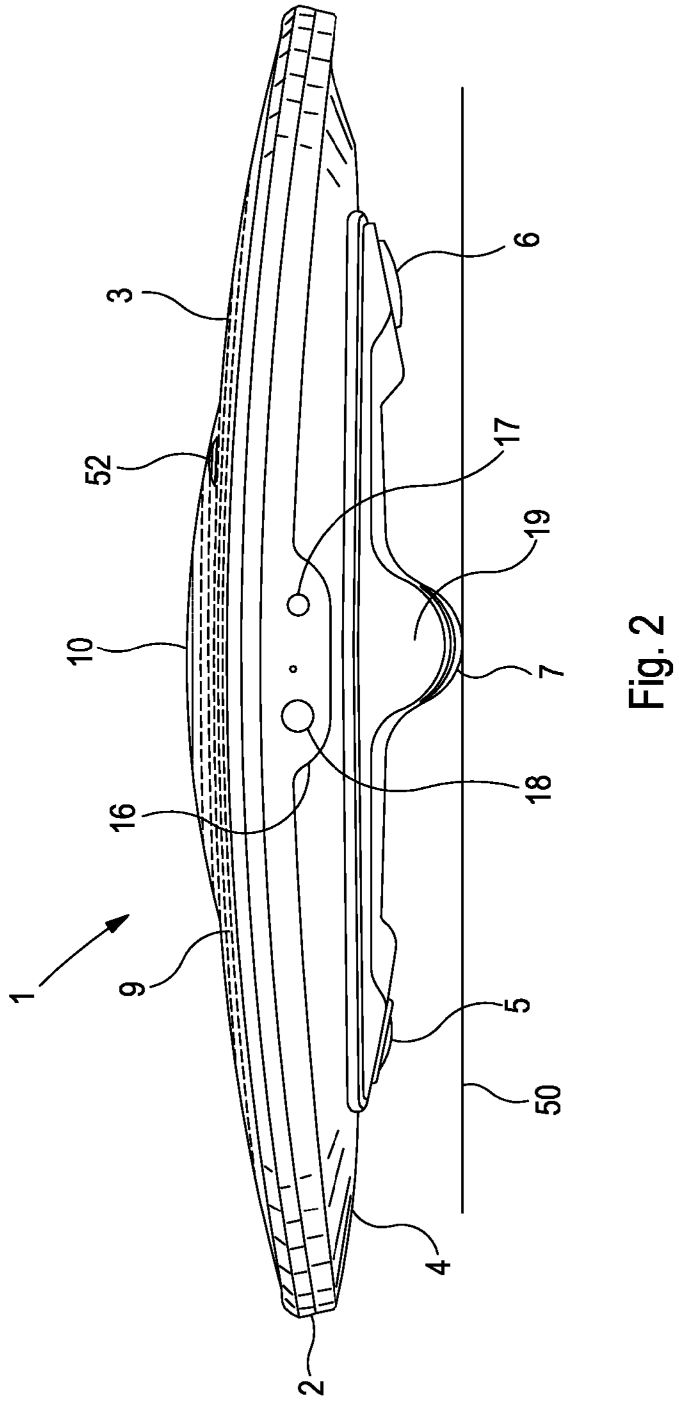
FIG. 2 is a side view of the device shown in FIG. 1.

FIG. 1 is a plan view of a device 1 for electrical stimulation of the plantar surfaces of the feet of a subject or user. The device 1 comprises a housing 2 that is generally in the form of a circular disc. The housing 2 incorporates a handle 15 to permit the device 1 to be easily moved by a user. FIG. 2 is a side view of the device 1 and it can be seen that the housing 1 has a generally convex curved upper surface 3 and a generally convex lower surface 4. Located on a side section 16 of the housing is a power adapter socket (or power jack) 18 to which a power adapter can be plugged in to provide power to a power supply unit 25 (see FIG. 3) located within the housing 2. The PSU 25 may incorporate a rechargeable power source, such as a rechargeable battery. Also located on the side section 16 is a socket 17 for connection of external contact pads which positioned on other parts of the body such as on the leg muscles.

The lower surface 4 includes a rest position stop 5 and a maximum position stop 6. Located between the stops 5, 6 are two rocker elements 7 (only one shown).

The upper surface 3 includes two electrical contact pads 8, 9 separated by a central display and control panel 10. The electrical contact pads 8, 9 have ribbing formed on them, as indicated in phantom on the pads 8, 9 and both the pads 8, 9 are formed from an electrically conducting material, such as a metal. For example, the pads 8, 9 may be formed from aluminium.

Mounted within (or inset into) each pad 8, 9 is an electrical contact 51, 52 respectively. Each of the electrical contacts 51, 52 are electrically isolated from the respective pad 8, 9 by an electrical insulator 53, 54 respectively. The electrical insulators 53, 54 may be formed from an electrically insulating material, such as a plastics material. The electrical contacts 51, 52 each have a contact surface that protrudes above the surface of the respective pad 8, 9. In this example, the electrical contacts 51, 52 comprise a partially spherical surface, such as hemi- spherical, with the partially spherical surface extending above the surface of the contact pads 8, 9.

However, the electrical contacts 51, 52 may be at least partially in the form of any curved surface, such as a portion of a spheroidal or ellipsoidal surface. Alternatively, or in addition, the electrical contacts 51, 52 may comprise at least partially planar surfaces that protrude above the surface of the contact pads 8, 9. For example, as an alternative to be being partially spherical shaped, the electrical contacts 51, 52 could be at least partially spheroidal, ellipsoidal, cylindrical, conical or frusto-conical shaped.

The display and control panel 10 includes a power button 11, up and down controls 12, 13 and a display 14. The power button 11, the up and down controls 12, 13 and the display 14 are shown in phantom as they are normally only visible when illuminated. The power button 11 and the up and down controls 12, 13 are touch sensitive areas of the zone 10 and so are shown in phantom.

As shown in FIG. 2, when the device 1 is positioned on a support surface 50, such as a floor or the ground, it is pivotable about pivot axis 19 from a rest position in which the rest stop 5 and rocker elements 7 contact the support surface, through an intermediate pivot position in which only the rocker elements 7 contact the support surface (as shown in FIG. 2), to a maximum pivot position in which the rocker elements 7 and the maximum position stop 6 contact the support surface 50.

Figure 3:
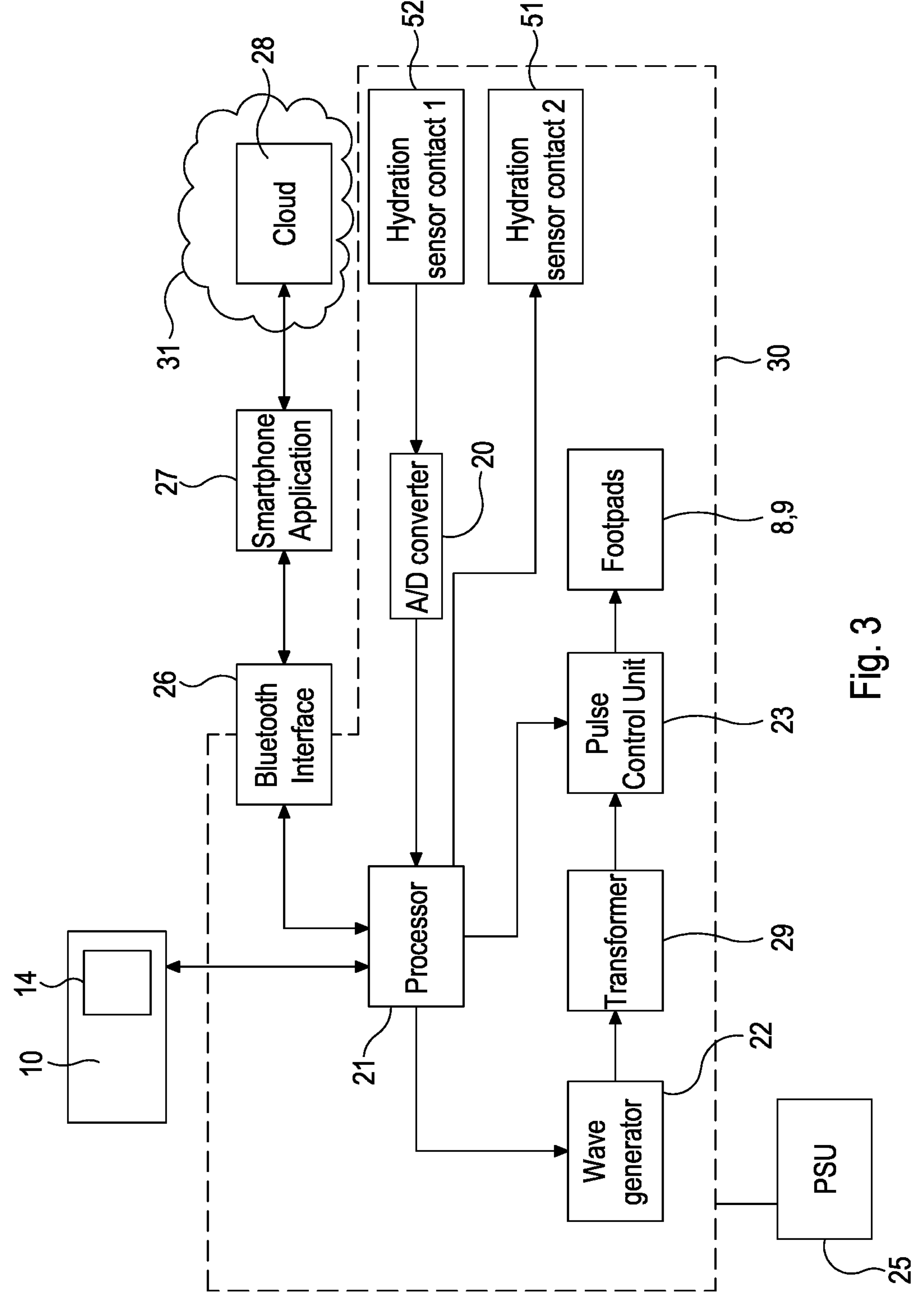
FIG. 3 is a block diagram illustrating the components of the apparatus for detecting electrical conductivity.

FIG. 3 is a block diagram of apparatus 30 located within the device 1 for controlling and feeding the electrical stimulation cycle voltage to the foot pads 8, 9 and for detecting electrical conductivity at the electrical contacts 51, 52. FIG. 3 also shows the power supply unit (PSU) 25 that is located within the housing 2 and provides electrical power to all the electrical components within the device 1, including the apparatus 30. A Bluetooth interface 26 provides a wireless communication interface between the apparatus 30 and smartphone 27 for data transmission between the device 1 and the smartphone 27. Also shown is a data storage server 28 located in the cloud on the Internet 31. The smartphone 27 can connect to the server 28 via an Internet connection. The Bluetooth interface 26 comprises a Bluetooth transceiver located within the device 1 and a Bluetooth transceiver located on the smartphone 27. The Bluetooth interface 26 is used to enable the apparatus 30 to communicate with the smartphone of a user. This can be used to enable the processor 21 to send information to the smartphone 27 to be displayed on the smartphone using a software application running on the smartphone and/or to enable control signals to be sent from the smartphone to the processor to control the operation of the apparatus 30.

The data storage server 28 can be used to download updates to the device 1 via the smartphone 7. For example, this could include one or more of software updates, configuration updates or data updates.

The PSU 25 is coupled to the power jack 18. Hence, the device 1 may be powered by either an external electrical power supply via the jack 18 or by the internal rechargeable batteries. However, it is possible that the device 1 may not include internal batteries and could be powered solely by an external power source via the jack 18. For example, the external power source is typically a 5V power adapter that connects to a 110V or 240V electrical mains power supply. The power adapter takes the 110V or 240V AC external main power supply and converts it to a 5V DC output voltage that is then fed to the power jack 18.

The apparatus 30 includes a processor 21. Typically, the processor 21 is a micro- controller unit (MCU). The processor 21 controls a wave generator 22 and a pulse control unit 23 and is also coupled to the Bluetooth transceiver on the device 1 and the control panel 10. In addition, the processor 21 has an output that is coupled to the electrical contact 51 and an input that receives a signal from an analogue to digital (A/D) converter 20 that receives an output signal from the electrical contact 52.

The wave generator 22 creates an alternating waveform from a 5V DC input from the PSU 25. This alternating waveform is then stepped up by transformer 29 before being fed to a pulse control unit 23 that generates, under control of the processor 21, the desired voltage pulse shape and duration. The voltage output from the pulse control unit 23 is then delivered across the footpads 8, 9 to provide the required electrical stimulation to the feet.

The processor 21 is configured to output a 1.7kHz square wave alternating voltage signal with a 3V amplitude to the electrical contact 51. The A/D converter receives a voltage signal from the electrical contact 52, converts it from an analogue signal to a digital signal with a value from 0 to 1024. The conversion is directly proportional to the analogue voltage signal received from the contact 52 with a 3V signal converted to value 1024 and a 0V signal converted to value 0 (zero). This digital converted signal is then output from the A/D converter 20 received as in input by the processor 21.

Figure 4:
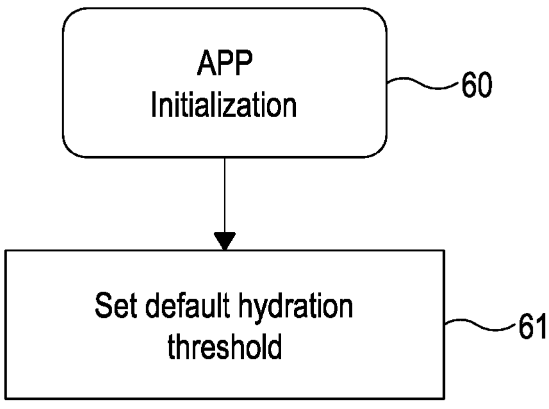
FIG. 4 is a flow diagram illustrating initialisation of a software application for use with the apparatus.

Prior to first use of the device 1, a user downloads a software application to their smartphone 27 or other mobile device, such as a tablet. The downloaded software application has a default electrical conductivity threshold value which is set when the software application is first opened. The first opening of the software application, initialises the software application and sets the default electrical conductivity threshold value (see FIG. 4).

Figure 5:
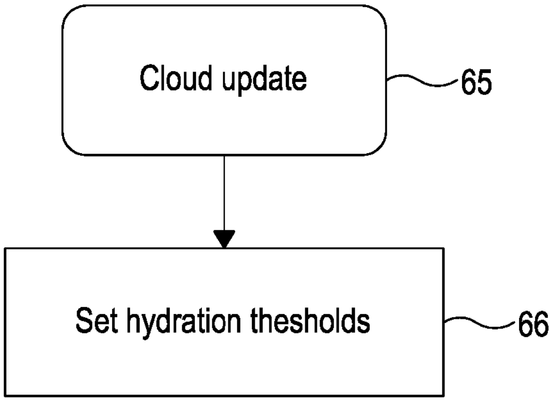
FIG. 5 is a flow diagram illustrating updating of the software application.

After initialisation of the software application, a cloud update 65 (see FIG. 5) over the internet 31 from the cloud server 28 can be used to update the software application, including updating 66 of the electrical conductivity threshold value. For example, updates to the electrical conductivity threshold may be necessary if testing data shows that a different threshold is more appropriate.

In use, a user positions the device on a support surface 50, such as on a floor in front of a seat that the user is going to sit on. If the device 1 does not have internal batteries, the user also connects the power input 18 to an external power supply. If the device 1 has internal batteries, the user can opt to either use the internal batteries, in which case it is not necessary to connect the power input 18 to an external power supply, or to use the external power supply.

The user then switches the device 1 on using switch 11. This causes the control panel 10 to illuminate. The user then also opens the application software on the smartphone 27 and the application software on the smartphone 27 connects with the device 1 through the Bluetooth® interface 26.

When the device 1 has started and the software application is connected, the user can then select a desired waveform using the control panel 10 or the software application on the smartphone 27.

Figure 7:
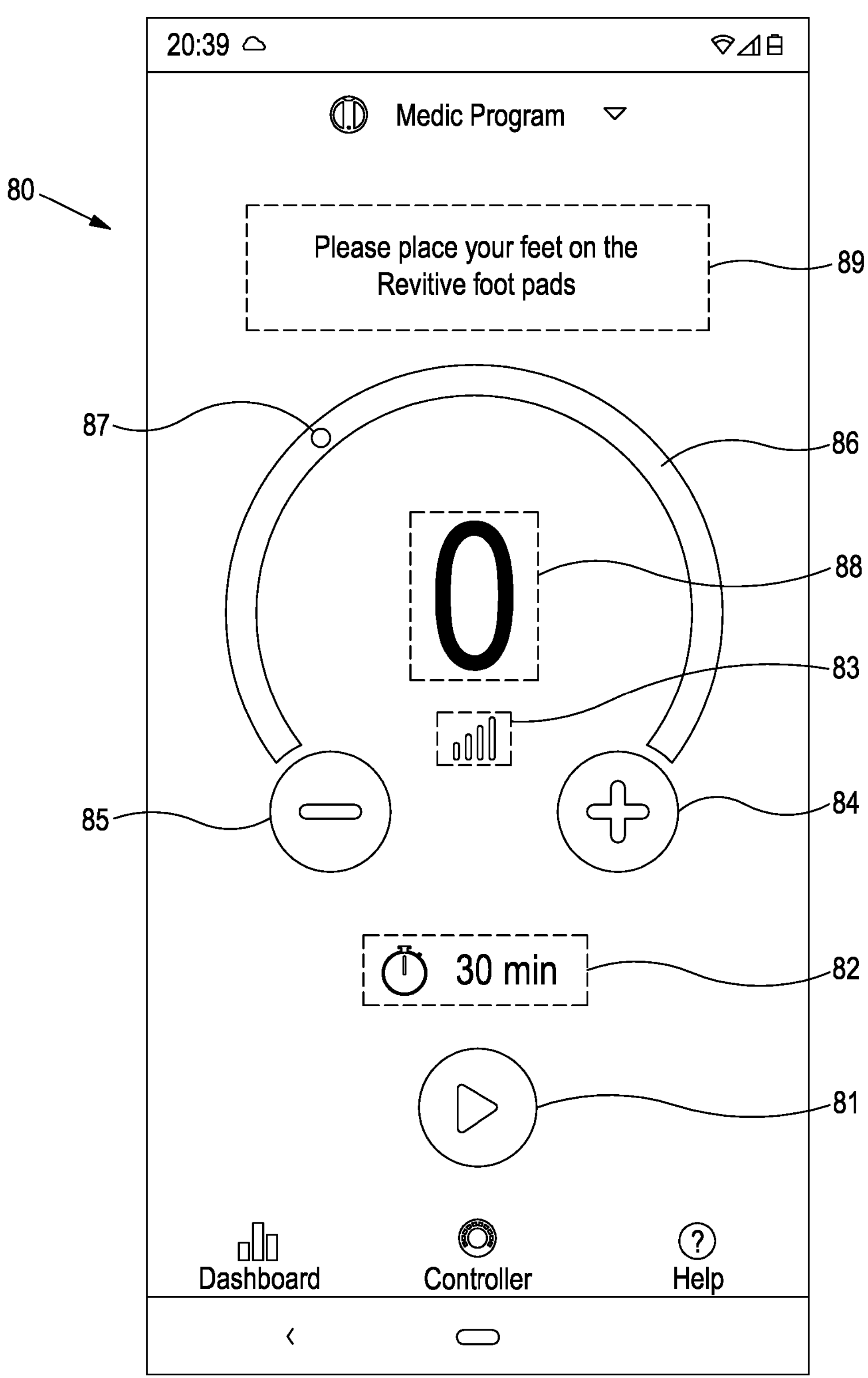
FIG. 7 shows an example of a first output from a display device for use with the apparatus.
Figure 8:
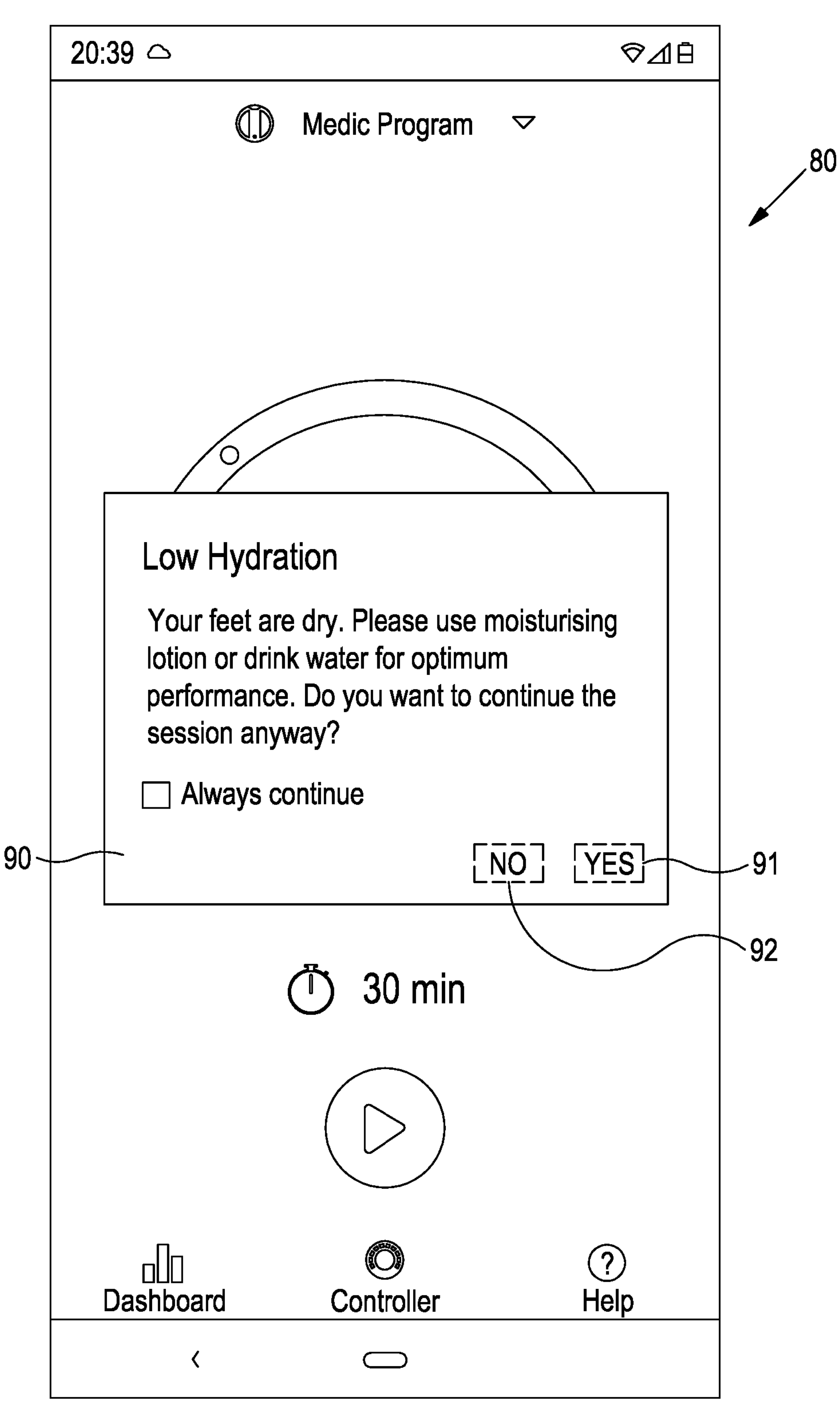
FIG. 8 shows an example of a second output from a display device for use with the apparatus.

After the waveform has been selected, the application on the smartphone 27 displays a user interface 80 (see FIG. 7) on a touchscreen of the smartphone 27. The user interface includes a start button 81, and indication 82 of duration of the stimulation and an icon 83 indicating the strength of the Bluetooth® connection with the device 1. The user interface 80 also includes a button 84 for increasing the strength of the stimulation and a button 85 for decreasing the strength of the stimulation. A point 87 on an arc-shaped graphic 86 indicates the relative strength of the stimulation and the numerical value of the stimulation is shown by numbers 88.

Also displayed on the user interface 80 is a message 89 instructing the user to place their feet on the contact pads 8, 9.

Figure 6:
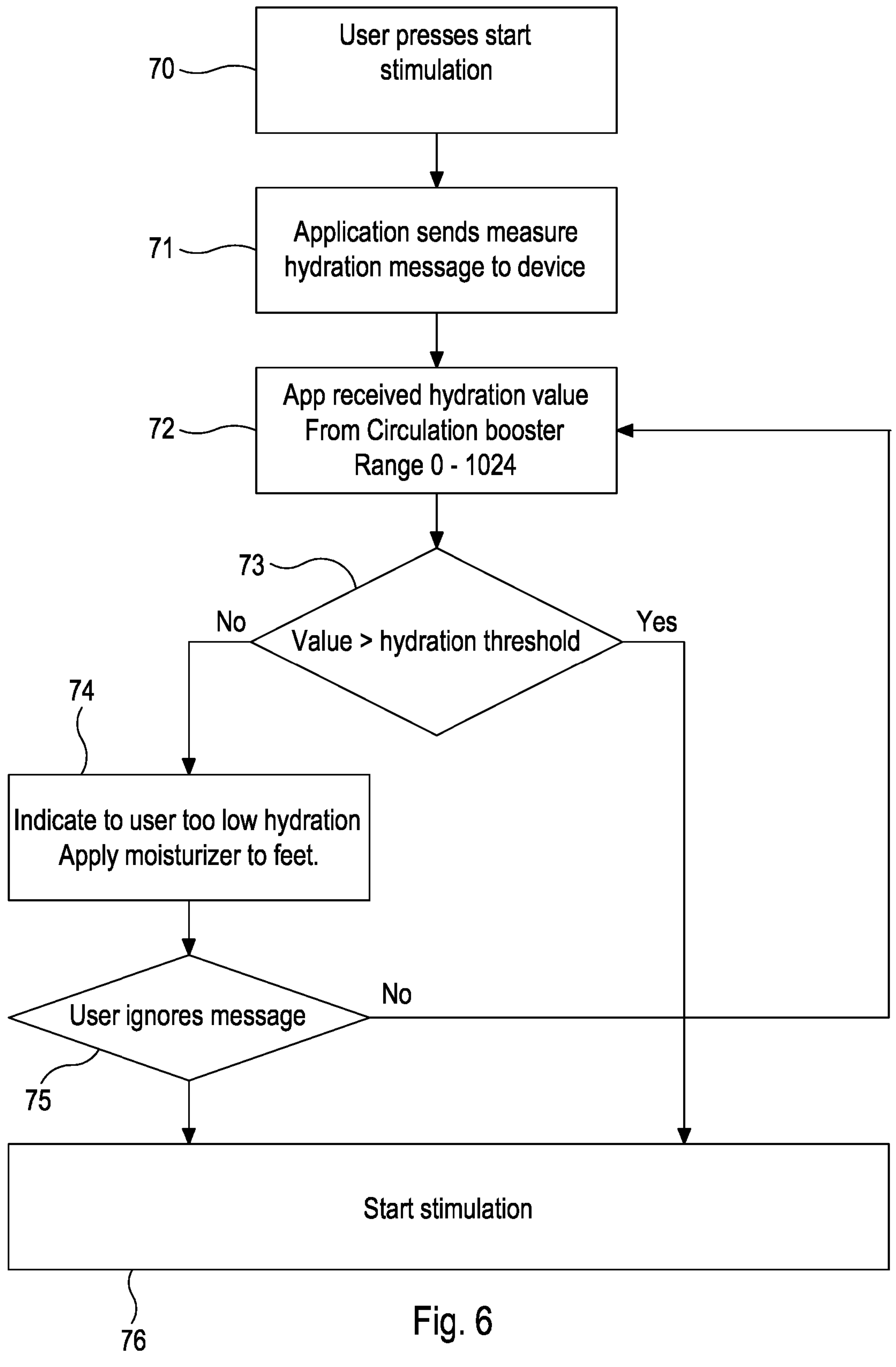
FIG. 6 is a flow diagram illustrating the operation of the apparatus.
Figure 9:
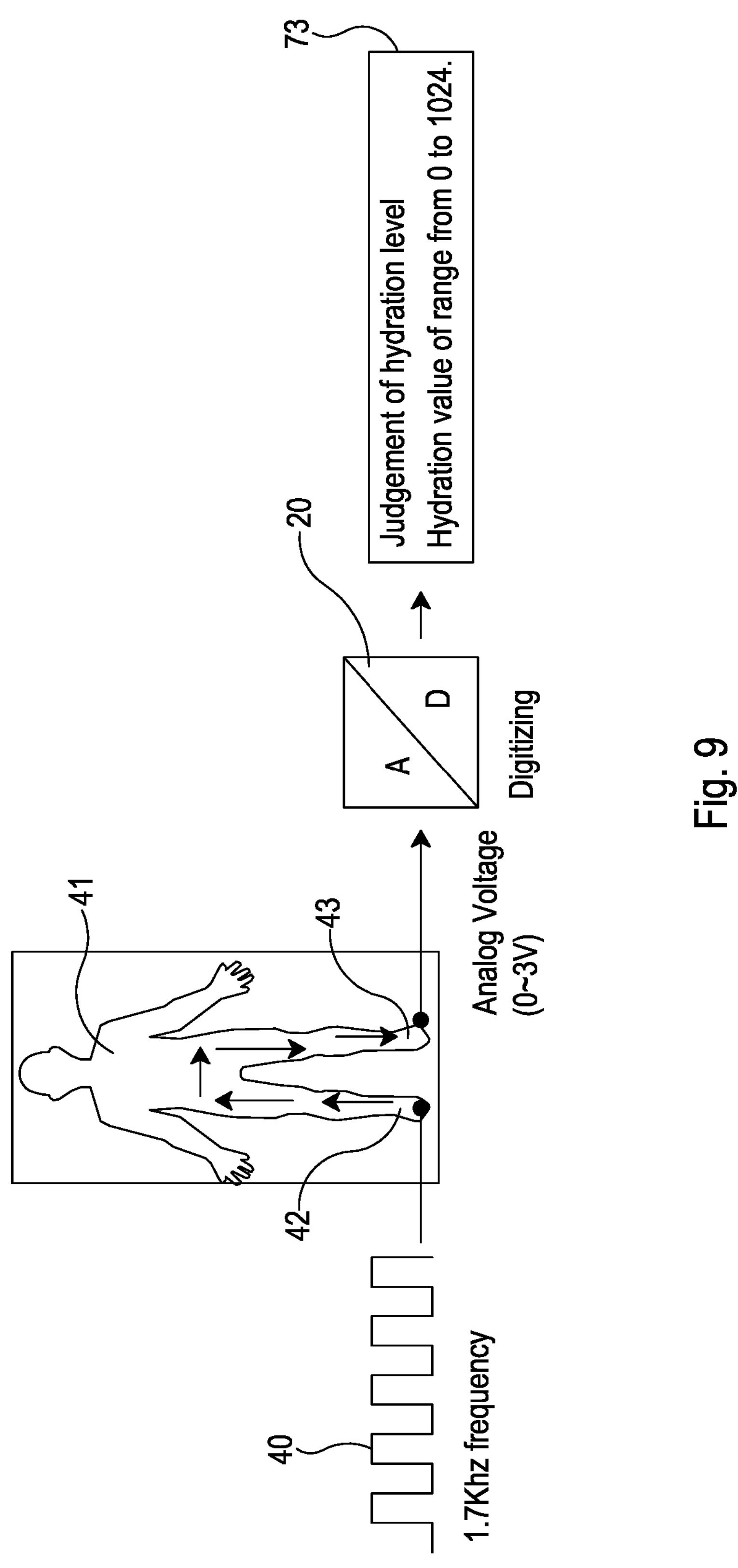
FIG. 9 is a schematic diagram showing operation of the apparatus in use.

After the user places one foot on each of the contact pads 8, 9 and presses 70 (see FIG. 6) the start button 81, the application on the smartphone 27 sends 71 a message to the processor 21 instructing it to measure hydration of the user. In response the processor 21 outputs a 1.7 kHz square wave alternating voltage 40 (see FIG. 9) with a 3V amplitude to the electrical contact 51. As the user's feet are on the pads 8, 9, the square wave voltage is applied to a foot 42 of a user 41 in contact with the pad 8. The contact 51 protrudes above the surface of the pad 8 to assist in ensuring there is an intimate contact between the electrical contact 51 and the plantar surface of the user's foot 42. The square wave voltage passes through the user's body and is picked up at the other electrical contact 52 at the user's other foot 43. The voltage signal received at the electrical contact 52 is output from the electrical contact 52 to the A/D converter 20 that converts the received voltage signal to a numeral value from 0 to 1024. The conversion is directly proportional to the amplitude of the received voltage signal. Therefore, a received voltage signal of 3V is converted to a value of 1024, a received voltage signal of 0V is converted to a value of 0 (zero) and a received voltage of 1.5V is converted to a value of 512.

If the received voltage is 3V this means in effect that there is a short circuit between the contacts 51, 52 and if the received voltage is 0V this in effect means that a user has not placed both feet on the pads 8, 9.

The digital value produced by the A/D converter 20 is then output to the processor 21 and the application on the smartphone 27 receives 72 the value from the processor 21 via the Bluetooth® wireless connection. The application on the smartphone 27 compares 73 the received value with a threshold value to determine whether there is a sufficiently high electrical conductivity between the electrical contacts 51, 52 to make an electrical stimulation voltage waveform applied to the pads 8, 9 effective. In effect this is a measure of the electrical conductivity of the user's body between the electrical contacts 51, 52. The inventors have found that there is a correlation between the electrical conductivity between the electrical contacts 51, 52 and the hydration of the user, so the electrical conductivity of the user's body between the electrical contacts 51, 52 is an indication of the hydration of the user.

Typically, a converted value from the A/D converter of 530 or greater indicates good electrical conductivity and therefore, good hydration of the user. A converted value of 200 or less indicates poor electrical conductivity and therefore, poor hydration of the user. Accordingly, a typical threshold used by the processor is approximately 250.

If the converted value received 72 by the application software is greater than the threshold (in this example less than or equal to 250), the application software then proceeds to start 76 the stimulation.

If the converted value received by the application software is less than or equal to the threshold (in this example less than or equal to 250), the application software causes a message 90 to be displayed on the user interface 80 informing the user that their feet are too dry and advising them to moisturise their feet and/or drink some water. The message 90 also asks the user whether they wish to continue the session. If the user selects "YES" 91 then the stimulation is started 76. If the user selects "NO" 92, the application software on the smartphone 27 sends 71 another request to the processor 21 to measure the electrical conductivity. The application software receives 72 the digitised measured value from the processor and compares 73 the new value with the threshold. If it still too low, the application software again displays 74 the message 90.

The application software will continue this loop to re-measure the electrical conductivity between the electrical contacts 51, 52 and compare it with the threshold until either (i) the measured value is when compared 73 with the threshold is greater than the threshold; or (ii) the user selects "YES" 91 to continue with the session. In either case (i) or (ii) the electrical stimulation will then start 76.

The inventor has appreciated that in some instances electrical stimulation of a subject may not be effective as the hydration of the subject may be too low. The inventor has realised that the hydration of the subject can be correlated to the electrical conductivity of the subject's body between the points on the body at which the electrical stimulation is applied. Where the electrical stimulation is applied to the plantar surfaces of the subject's feet, the electrical conductivity between the subject's feet can be measured to give an indication of the hydration of the subject and whether electrical stimulation is likely to be effective based on the measured electrical conductivity.

The invention has the advantages of being able to detect whether the electrical conductivity of the user's body between the electrical contacts 51, 52 is too low for effective electrical stimulation to occur and to also advise the user to moisturise their feet and/or to drink water to hydrate themselves.

The invention claimed is:

1. Apparatus for detecting electrical conductivity between a subject and a device for electrical stimulation of the subject, the apparatus comprising:

(i) a first electrical contact adapted to contact skin of a subject in a first location, in use;

(ii) a second electrical contact adapted to contact the skin of the subject in a second location, in use;

(iii) a processor having an output coupled to the first electrical contact and an input coupled to the second electrical contact;

(iv) an output device coupled to the processor; and wherein the processor is configured to output an alternating voltage signal to the first electrical contact and to receive a response signal from the second electrical contact; and the processor being further configured to either: (a) send an output signal to the output device in response to the received response signal, the output signal corresponding to the received response signal and being indicative of the electrical conductivity between the device and the subject, in use; or (b) send an output signal to the output device when a voltage amplitude of the response signal received by the processor is below a threshold, the output signal being indicative that the electrical conductivity between the subject and the device is below the threshold;

the apparatus further comprising electrical stimulation means that is adapted to apply an electrical stimulation voltage to muscles of a body part of the subject, in use;

wherein the electrical stimulation means comprises first and second electrical stimulation contact surfaces;

wherein the first electrical contact is located within the first electrical stimulation contact surface and the second electrical contact is located within the second electrical stimulation contact surface; and wherein the first electrical contact is electrically isolated from the first electrical stimulation contact surface and the second electrical contact is electrically isolated from the second electrical stimulation contact surface.

2. Apparatus according to claim 1, further comprising an analogue to digital (A/D) convertor means, the A/D convertor means receiving the response signal from the second electrical contact, converting the response signal to a digital signal and sending the digital signal to the processor.

3. Apparatus according to claim 1, wherein the alternating voltage signal has an amplitude of less than 10V.

4. Apparatus according to claim 1, wherein the alternating voltage signal comprises a square wave signal.

5. Apparatus according to claim 1, wherein the alternating voltage signal has a frequency of from 500 Hz to 100 kHz.

6. Apparatus according to claim 1, wherein the output device comprises at least one of: a visual display device; an audible signal output device; a haptic signal output device; and a wireless data signal output device.

7. Apparatus according to claim 1, wherein the processor sends the output signal to the output device if the voltage amplitude of the response signal received by the processor is below a threshold, and the threshold corresponds to an amplitude of the response signal that is less than 50% of the output alternating voltage signal.

8. Apparatus according to claim 1, wherein the first and second electrical contacts are adapted to contact the skin of the subject such that the first and second locations are on different limbs of the subject.

9. Apparatus according to claim 8, wherein the first and second locations are on different lower legs of the subject.

10. The apparatus according to claim 1, wherein at least a portion of the first and second electrical contacts extend above the respective first and second electrical stimulation contact surfaces.

11. The apparatus according to claim 1, wherein the device is adapted to apply electrical stimulation to the feet of a subject, in use.

12. The apparatus according to claim 11, wherein the first and second electrical stimulation contact surfaces are each adapted to contact a respective plantar surface of a foot of the subject, in use.

13. The apparatus according to claim 1, wherein the electrical stimulation means are adapted to stimulate at least one of the leg and foot muscles of the subject.

14. A system comprising an apparatus in accordance with claim 1 and a remote device comprising a remote wireless data input device, a remote processor and a remote output device; wherein the processor sends the output signal to the output device in response to the received response signal, the output device comprises a wireless data output device and the output signal comprises a wireless data signal emitted by the wireless data output device; and the remote wireless data input device is adapted to receive the wireless data signal and to send the received signal to the remote processor, and if the received signal is less than a threshold, the remote processor outputs a remote output signal to the remote output device, the remote output signal being indicative that the electrical conductivity between the subject and the device is too low.

15. A system according to claim 14, wherein in response to the remote output signal, the remote output device generates a remote user output signal that the electrical conductivity between the subject and the device is below the threshold.

16. A method of detecting electrical conductivity between a subject and a device for electrical stimulation of the subject, the method comprising:

(i) contacting a first electrical contact against skin of a subject in a first location;

(ii) contacting a second electrical contact against the skin of the subject in a second location;

(iii) applying an alternating voltage signal to the first electrical contact;

(iv) receiving a response signal at the second electrical contact;

(v) transmitting the response signal to a processor; and wherein the processor is configured to output an alternating voltage signal to the first electrical contact and to receive a response signal from the second electrical contact; and the processor being further configured to either: (a) send an output signal to the output device in response to the received response signal, the output signal corresponding to the received response signal and being indicative of the electrical conductivity between the device and the subject, in use; or (b) send an output signal to the output device if a voltage amplitude of the response signal received by the processor is below a threshold, the output signal being indicative that the electrical conductivity between the subject and the device is below the threshold;

the device for electrical stimulation of the subject comprising electrical stimulation means that is adapted to apply an electrical stimulation voltage to muscles of a body part of the subject, in use;

wherein the electrical stimulation means comprises first and second electrical stimulation contact surfaces;

wherein the first electrical contact is located within the first electrical stimulation contact surface and the second electrical contact is located within the second electrical stimulation contact surface; and wherein the first electrical contact is electrically isolated from the first electrical stimulation contact surface and the second electrical contact is electrically isolated from the second electrical stimulation contact surface.

* * * * *